United States Patent [19]

Dawson et al.

[11] Patent Number: 5,688,664

[45] Date of Patent: Nov. 18, 1997

[54] THROMBIN ACTIVATABLE PLASMINOGEN ANALOGUES

[75] Inventors: Keith Martyn Dawson; Richard James Gilbert; Michael George Hunter, all of Oxford, England

[73] Assignee: British Bio-Technology Ltd., England

[21] Appl. No.: 147,000

[22] Filed: Oct. 29, 1993

Related U.S. Application Data

[63] Continuation-in-part of Ser. No. 854,603, Jun. 4, 1992.

[30] Foreign Application Priority Data

Dec. 7, 1990 [WO] WIPO .............. PCT/GB90/01912
Oct. 29, 1992 [GB] United Kingdom .............. 9222758

[51] Int. Cl.⁶ .............. A61K 38/48; C12N 9/68; C12P 21/00
[52] U.S. Cl. .............. 435/69.2; 435/217; 424/94.64
[58] Field of Search .............. 435/217, 69.2; 424/94.64

[56] References Cited

U.S. PATENT DOCUMENTS 5,200,340  4/1993  Foster et al. .............. 424/94.64

FOREIGN PATENT DOCUMENTS

PCT/GB90/
01912  6/1991  WIPO .

OTHER PUBLICATIONS

Ni, F., et al., (1989), *Biochemistry*, vol. 28, pp. 3082–3094.
Gailani, D. and Broze, G.J. (1991), *Science*, vol. 253, pp. 909–912.
Naski et al., (1991), *Biochemistry*, vol. 30, pp. 934–941.
Ichinose et al., (1986), *J. Biol. Chem.*, vol. 261, pp. 3486–3489.
Forsgren et al. (1987), *FEBS Letters*, vol. 213, pp. 254–260.
Bok, R.A. and Mangel, W.F. (1985), *Biochemistry*, vol. 24, pp. 3279–3286.
Madison, E.L. et al., (1989), *Nature*, vol. 339, pp. 721–724.
Naito, Koji et al., (1990), *J. Biol. Chem.*, vol. 266, pp. 7353–7358.
Dawson et al., *J. Biol. Chem.* 269:15989–15992 (1994).
Chang, *Eur. J. Biochem.* 151:217–224 (1985).
Lehninger, *Principles of Biochemistry*, Worth Pulishers Inc., New York, NY, 1982, pp. 100–103.

*Primary Examiner*—Robert A. Wax
*Assistant Examiner*—Eric Grimes
*Attorney, Agent, or Firm*—Banner & Witcoff, Ltd.

[57] ABSTRACT

A plasminogen analogue activatable by thrombin to have plasmin activity which contains the cleavage site sequence (SEQ ID NO: 23):

Xaa Xaa Pro Arg Xaa Xaa
1                 5 where Xaa at position 1 represents P4; Xaa at position 2 represents P3; Xaa at position 5 represents P1'; and Xaa at position 6 represents P2' where P3 is a basic amino acid residue, P4 is a hydrophobic amino acid residue and each of P1' and P2' is independently a non-acidic amino acid residue, said site being cleavable by thrombin between Arg and P1'.

22 Claims, 3 Drawing Sheets

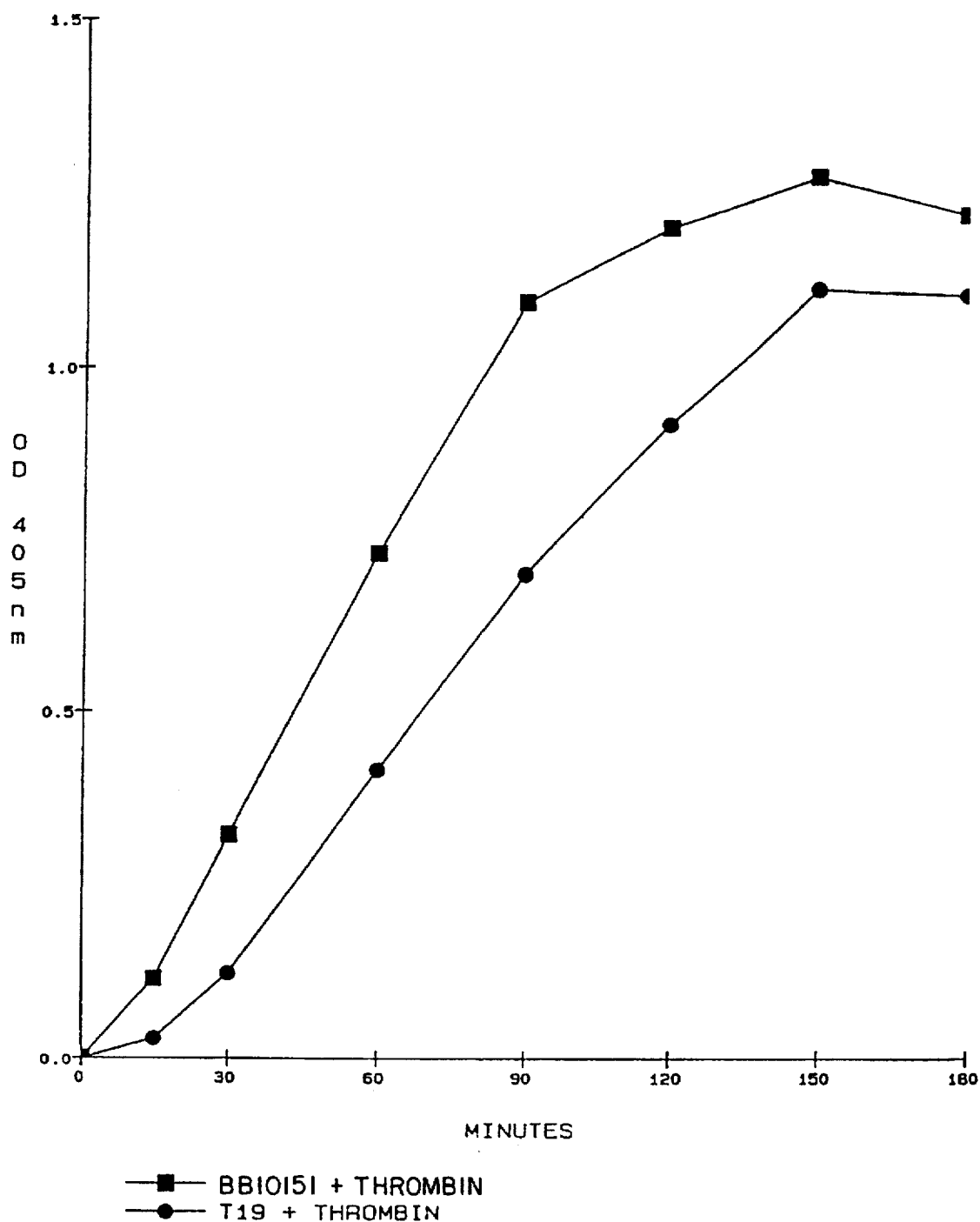

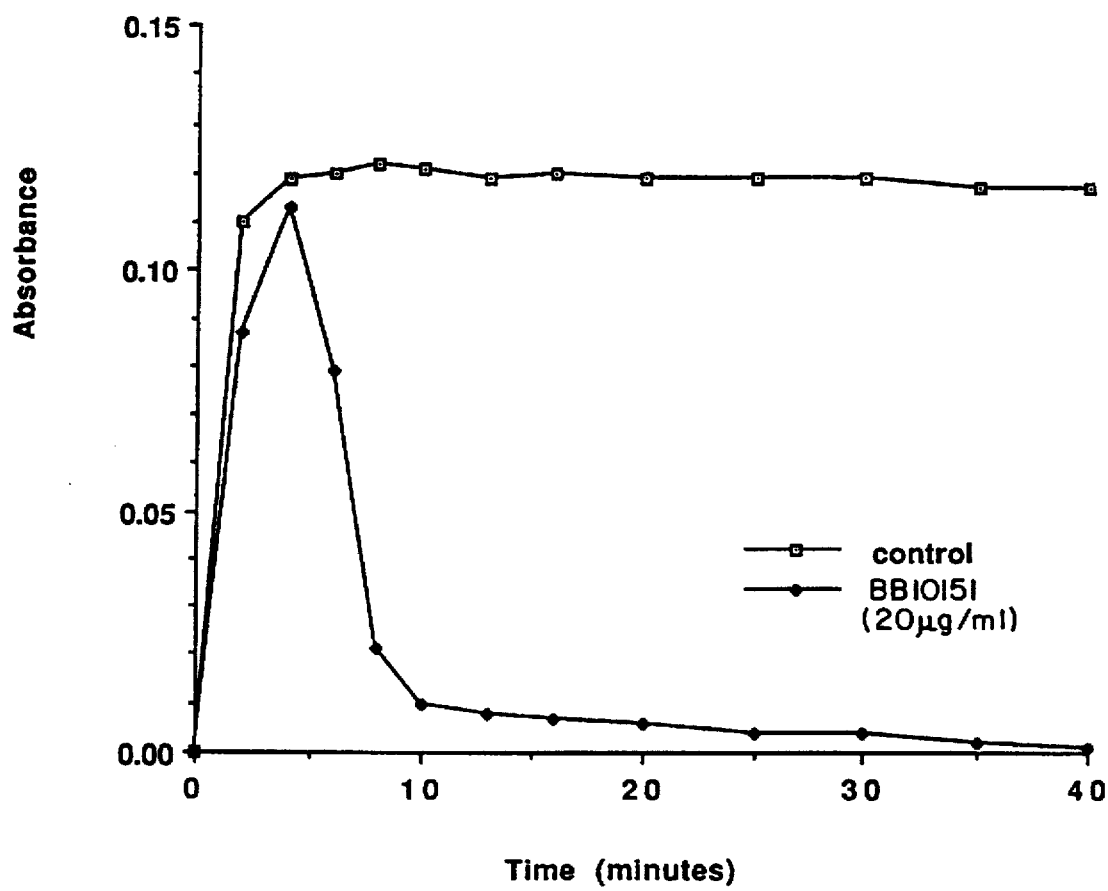

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 9 amino acids ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: BB10151
        ( B ) LOCATION:
        ( D ) OTHER INFORMATION:

( x i ) SEQUENCE DESCRIPTION: SEQ ID NO:1:

Thr Thr Lys Ile Lys Pro Arg Ile Xaa
 1           5

( 2 ) INFORMATION FOR SEQ ID NO:2:

( i ) SEQUENCE CHARACTERISTICS:
        ( A ) LENGTH: 230 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Domain
        ( B ) LOCATION: 1-230
        ( D ) OTHER INFORMATION: Serine Protease Domain of
              wild type plasmin ( x i ) SEQUENCE DESCRIPTION: SEQ ID NO:2:

Val Val Gly Gly Cys Val Ala His Pro His Ser Trp Pro Trp Gln
 1           5                  10                  15

Val Ser Leu Arg Thr Arg Phe Gly Met His Phe Cys Gly Gly Thr
            20                  25                  30

Leu Ile Ser Pro Glu Trp Val Leu Thr Ala Ala His Cys Leu Glu
                35                  40                  45

Lys Ser Pro Arg Pro Ser Ser Tyr Lys Val Ile Leu Gly Ala His
                50                  55                  60

Gln Glu Val Asn Leu Glu Pro His Gly Gln Glu Ile Glu Val Ser
                65                  70                  75

Arg Leu Phe Leu Glu Pro Thr Arg Lys Asp Ile Ala Leu Leu Lys
                80                  85                  90

Leu Ser Ser Pro Ala Val Ile Thr Asp Lys Val Ile Pro Ala Cys
                95                  100                 105

Leu Pro Ser Pro Asn Tyr Val Val Ala Asp Arg Thr Glu Cys Phe
                110                 115                 120

Ile Thr Gly Trp Gly Glu Thr Gln Gly Thr Phe Gly Ala Gly Leu
                125                 130                 135

Leu Lys Glu Ala Gln Leu Pro Val Ile Glu Asn Lys Val Cys Asn
                140                 145                 150

Arg Tyr Glu Phe Leu Asn Gly Arg Val Gln Ser Thr Glu Leu Cys
                155                 160                 165

Ala Gly His Leu Ala Gly Gly Thr Asp Ser Cys Gln Gly Asp Ser
                170                 175                 180

Gly Gly Pro Leu Val Cys Phe Glu Lys Asp Lys Tyr Ile Leu Gln
                185                 190                 195

Gly Val Thr Ser Trp Gly Leu Gly Cys Ala Arg Pro Asn Lys Pro
                200                 205                 210

Gly Val Tyr Val Arg Val Ser Arg Phe Val Thr Trp Ile Glu Gly
                215                 220                 225

Val Met Arg Asn Asn
            230

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Misc_feature
        (B) LOCATION: 1..24
        (D) OTHER INFORMATION: mutagenesis oligonucleotide (xi) SEQUENCE DESCRIPTION: SEQ ID NO:3:

CTTGGGGACT TCTTCAAGCA GTGG          24

(2) INFORMATION FOR SEQ ID NO:4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..48
        (D) OTHER INFORMATION: mutagenesis oligonucleotide (xi) SEQUENCE DESCRIPTION: SEQ ID NO:4:

CACCCCCCTA CGATTCTAGG TTTAATTTTA GTTGTACATT TCTTCGGC    48

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY:
        (B) LOCATION:
        (D) OTHER INFORMATION: mutagenesis oligonucleotide (xi) SEQUENCE DESCRIPTION: SEQ ID NO:5:

GTTCGAGATT CACTTTTGG TGTGCAC          27

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: BB10150
        (B) LOCATION:
        (D) OTHER INFORMATION:

(xi) SEQUENCE DESCRIPTION: SEQ ID NO:6:

```
Ala  Val  Val  Pro  Arg  Val  Val  Gly  Gly  Ala
 1              5                        10
```

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:7:

```
CTAGGTACAA CCGCTTTCTT CGGCT                                    25
```

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:8:

```
GGTGGGCCAC CGCCCCCCCC AC                                       22
```

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Cys  Val  Val  Pro  Arg  Val  Val  Gly  Gly  Cys
 1              5                        10
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: BB10156
        ( B ) LOCATION:
        ( D ) OTHER INFORMATION:

( x i ) SEQUENCE DESCRIPTION: SEQ ID NO:10:

```
Ala  Gly  Gln  Lys  Thr  Leu  Arg  Pro  Arg  Val  Val  Gly  Gly  Ala
 1              5                        10
```

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: BB10158
        ( B ) LOCATION:
        ( D ) OTHER INFORMATION:

( x i ) SEQUENCE DESCRIPTION: SEQ ID NO:11:

```
Ala  Thr  Thr  Lys  Ile  Lys  Pro  Arg  Ile  Val  Gly  Gly  Ala
 1                  5                       10
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: BB10170
        ( B ) LOCATION:
        ( D ) OTHER INFORMATION:

( x i ) SEQUENCE DESCRIPTION: SEQ ID NO:12:

```
Ala  Leu  Arg  Pro  Arg  Val  Val  Gly  Gly  Ala
 1                  5                       10
```

( 2 ) INFORMATION FOR SEQ ID NO:13:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:13:

CAACCCTAGG TCTAAGTGTT TTCTGACCCG CTTTCTTCG                     39

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:14:

CAACCCTAGG TTTGATCTTC GTTGTCGCTT TCTTCG                                    36

( 2 ) INFORMATION FOR SEQ ID NO:15:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY:
      ( B ) LOCATION:
      ( D ) OTHER INFORMATION: mutagenesis oligonucleotide ( x i ) SEQUENCE DESCRIPTION: SEQ ID NO:15:

CACAACCCTA GGTCTAAGCG CTTTCTTCGG                                           30

( 2 ) INFORMATION FOR SEQ ID NO:16:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: BB10169
      ( B ) LOCATION:
      ( D ) OTHER INFORMATION:

( x i ) SEQUENCE DESCRIPTION: SEQ ID NO:16:

Cys Val Glu Leu Gln Gly Ile Lys Pro Arg Ile Val Gly Gly Cys
1               5                   10                  15

( 2 ) INFORMATION FOR SEQ ID NO:17:

( i ) SEQUENCE CHARACTERISTICS:
      ( A ) LENGTH: 42 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY:
      ( B ) LOCATION:
      ( D ) OTHER INFORMATION: mutagenesis oligonucleotide ( x i ) SEQUENCE DESCRIPTION: SEQ ID NO:17:

GATTCTAGGT TTAATGCCCT GCAGTTCCAC ACATTTCTTC GG                             42

( 2 ) INFORMATION FOR SEQ ID NO:18:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: BB10171
      ( B ) LOCATION:
      ( D ) OTHER INFORMATION:

( x i ) SEQUENCE DESCRIPTION: SEQ ID NO:18:

Cys Val Glu Leu Gln Gly Leu Arg Pro Arg Val Val Gly Gly Cys
1               5                   10                  15

( 2 ) INFORMATION FOR SEQ ID NO:19:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:19:

CACCCCCCTA CCACTCTGGG TCTCAGGCCC TGCAGTTCC        39

( 2 ) INFORMATION FOR SEQ ID NO:20:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:20:

CCCTGCGGAG AGTTGGATGG ATTCCTGC        28

( 2 ) INFORMATION FOR SEQ ID NO:21:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:21:

GAAGTGCATT CCTCTCCTCG TACGAAG        27

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY:
        ( B ) LOCATION:
        ( D ) OTHER INFORMATION: mutagenesis oligonucleotide ( x i ) SEQUENCE DESCRIPTION: SEQ ID NO:22:

CCACAGAAGT GTCTTCCAAA CCTCG     25

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( D ) OTHER INFORMATION: Plasminogen analogue thrombin
            cleavable site sequence where Xaa at position 1
            represents P4; Xaa at position 2 represents P3;
            Xaa at position 5 represents P1'; and Xaa at
            position 6 represents P2'.

( x i ) SEQUENCE DESCRIPTION: SEQ ID NO:23:

Xaa Xaa Pro Arg Xaa Xaa
1               5

( 2 ) INFORMATION FOR SEQ ID NO:24:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY:
        ( B ) LOCATION:
        ( D ) OTHER INFORMATION: alpha- thrombin cleavage site where
            Xaa at position 1 represents P2 and Xaa at position 3
            represents P1'.

( x i ) SEQUENCE DESCRIPTION: SEQ ID NO:24:

Xaa Arg Xaa
1

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Val Glu Leu Gln Gly Val Val Pro
1               5

( 2 ) INFORMATION FOR SEQ ID NO:26:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY:
    ( B ) LOCATION:
    ( D ) OTHER INFORMATION: Plasminogen analogue cleavage site
        where Xaa at position 8 represents P1' and Xaa at
        position 7 represents P2'.

( x i ) SEQUENCE DESCRIPTION: SEQ ID NO:26:

```
Thr  Thr  Lys  Ile  Lys  Pro  Arg  Xaa  Xaa
 1              5
```

( 2 ) INFORMATION FOR SEQ ID NO:27:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Leu  Arg  Pro  Arg
 1
```

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Cys  Thr  Thr  Lys  Ile  Lys  Pro  Arg  Ile  Val  Gly  Gly  Cys
 1              5                        10
```

( 2 ) INFORMATION FOR SEQ ID NO:29:

( i ) SEQUENCE CHARACTERISTICS:
        ( A ) LENGTH: 810 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Met  Glu  His  Lys  Glu  Val  Val  Leu  Leu  Leu  Leu  Phe  Leu  Lys  Ser
-19            -15                 -10                      -5

Gly  Gln  Gly  Glu  Pro  Leu  Asp  Asp  Tyr  Val  Asn  Thr  Gln  Gly  Ala  Ser
                1              5                        10

Leu  Phe  Ser  Val  Thr  Lys  Lys  Gln  Leu  Gly  Ala  Gly  Ser  Ile  Glu  Glu
     15                 20                           25

Cys  Ala  Ala  Lys  Cys  Glu  Glu  Asp  Glu  Glu  Phe  Thr  Cys  Arg  Ala  Phe
 30                 35                      40                            45

Gln  Tyr  His  Ser  Lys  Glu  Gln  Gln  Cys  Val  Ile  Met  Ala  Glu  Asn  Arg
               50                      55                            60

Lys  Ser  Ser  Ile  Ile  Ile  Arg  Met  Arg  Asp  Val  Val  Leu  Phe  Glu  Lys
                65                      70                      75

Lys  Val  Tyr  Leu  Ser  Glu  Cys  Lys  Thr  Gly  Asn  Gly  Lys  Asn  Tyr  Arg
          80                      85                      90

Gly  Thr  Met  Ser  Lys  Thr  Lys  Asn  Gly  Ile  Thr  Cys  Gln  Lys  Trp  Ser
          95                      100                     105
```

| | | | | | | | | | | | | | | |
|---|---|---|---|---|---|---|---|---|---|---|---|---|---|---|
| Ser | Thr | Ser | Pro | His | Arg | Pro | Arg | Phe | Ser | Pro | Ala | Thr | His | Pro | Ser |
| 110 | | | | | 115 | | | | | 120 | | | | | 125 |
| Glu | Gly | Leu | Glu | Glu | Asn | Tyr | Cys | Arg | Asn | Pro | Asp | Asn | Asp | Pro | Gln |
| | | | | 130 | | | | | 135 | | | | | 140 | |
| Gly | Pro | Trp | Cys | Tyr | Thr | Thr | Asp | Pro | Glu | Lys | Arg | Tyr | Asp | Tyr | Cys |
| | | | 145 | | | | | 150 | | | | | 155 | | |
| Asp | Ile | Leu | Glu | Cys | Glu | Glu | Glu | Cys | Met | His | Cys | Ser | Gly | Glu | Asn |
| | | | 160 | | | | 165 | | | | | 170 | | | |
| Tyr | Asp | Gly | Lys | Ile | Ser | Lys | Thr | Met | Ser | Gly | Leu | Glu | Cys | Gln | Ala |
| | | 175 | | | | 180 | | | | | 185 | | | | |
| Trp | Asp | Ser | Gln | Ser | Pro | His | Ala | His | Gly | Tyr | Ile | Pro | Ser | Lys | Phe |
| 190 | | | | | 195 | | | | | 200 | | | | | 205 |
| Pro | Asn | Lys | Asn | Leu | Lys | Lys | Asn | Tyr | Cys | Arg | Asn | Pro | Asp | Arg | Glu |
| | | | | 210 | | | | | 215 | | | | | 220 | |
| Leu | Arg | Pro | Trp | Cys | Phe | Thr | Thr | Asp | Pro | Asn | Lys | Arg | Trp | Glu | Leu |
| | | | 225 | | | | | 230 | | | | | 235 | | |
| Cys | Asp | Ile | Pro | Arg | Cys | Thr | Thr | Pro | Pro | Pro | Ser | Ser | Gly | Pro | Thr |
| | | | 240 | | | | | 245 | | | | | 250 | | |
| Tyr | Gln | Cys | Leu | Lys | Gly | Thr | Gly | Glu | Asn | Tyr | Arg | Gly | Asn | Val | Ala |
| | | 255 | | | | | 260 | | | | | 265 | | | |
| Val | Thr | Val | Ser | Gly | His | Thr | Cys | Gln | His | Trp | Ser | Ala | Gln | Thr | Pro |
| 270 | | | | | 275 | | | | | 280 | | | | | 285 |
| His | Thr | His | Asn | Arg | Thr | Pro | Glu | Asn | Phe | Pro | Cys | Lys | Asn | Leu | Asp |
| | | | | 290 | | | | | 295 | | | | | 300 | |
| Glu | Asn | Tyr | Cys | Arg | Asn | Pro | Asp | Gly | Lys | Arg | Ala | Pro | Trp | Cys | His |
| | | | 305 | | | | | 310 | | | | | 315 | | |
| Thr | Thr | Asn | Ser | Gln | Val | Arg | Trp | Glu | Tyr | Cys | Lys | Ile | Pro | Ser | Cys |
| | | | 320 | | | | | 325 | | | | | 330 | | |
| Asp | Ser | Ser | Pro | Val | Ser | Thr | Glu | Gln | Leu | Ala | Pro | Thr | Ala | Pro | Pro |
| | | 335 | | | | | 340 | | | | | 345 | | | |
| Glu | Leu | Thr | Pro | Val | Val | Gln | Asp | Cys | Tyr | His | Gly | Asp | Gly | Gln | Ser |
| 350 | | | | | 355 | | | | | 360 | | | | | 365 |
| Tyr | Arg | Gly | Thr | Ser | Ser | Thr | Thr | Thr | Thr | Gly | Lys | Lys | Cys | Gln | Ser |
| | | | | 370 | | | | | 375 | | | | | 380 | |
| Trp | Ser | Ser | Met | Thr | Pro | His | Arg | His | Gln | Lys | Thr | Pro | Glu | Asn | Tyr |
| | | | 385 | | | | | 390 | | | | | 395 | | |
| Pro | Asn | Ala | Gly | Leu | Thr | Met | Asn | Tyr | Cys | Arg | Asn | Pro | Asp | Ala | Asp |
| | | | 400 | | | | | 405 | | | | | 410 | | |
| Lys | Gly | Pro | Trp | Cys | Phe | Thr | Thr | Asp | Pro | Ser | Val | Arg | Trp | Glu | Tyr |
| | | 415 | | | | | 420 | | | | | 425 | | | |
| Cys | Asn | Leu | Lys | Lys | Cys | Ser | Gly | Thr | Glu | Ala | Ser | Val | Val | Ala | Pro |
| 430 | | | | | 435 | | | | | 440 | | | | | 445 |
| Pro | Pro | Val | Val | Leu | Leu | Pro | Asp | Val | Glu | Thr | Pro | Ser | Glu | Glu | Asp |
| | | | | 450 | | | | | 455 | | | | | 460 | |
| Cys | Met | Phe | Gly | Asn | Gly | Lys | Gly | Tyr | Arg | Gly | Lys | Arg | Ala | Thr | Thr |
| | | | 465 | | | | | 470 | | | | | 475 | | |
| Val | Thr | Gly | Thr | Pro | Cys | Gln | Asp | Trp | Ala | Ala | Gln | Glu | Pro | His | Arg |
| | | | 480 | | | | | 485 | | | | | 490 | | |
| His | Ser | Ile | Phe | Thr | Pro | Glu | Thr | Asn | Pro | Arg | Ala | Gly | Leu | Glu | Lys |
| | | 495 | | | | | 500 | | | | | 505 | | | |
| Asn | Tyr | Cys | Arg | Asn | Pro | Asp | Gly | Asp | Val | Gly | Gly | Pro | Trp | Cys | Tyr |
| 510 | | | | | 515 | | | | | 520 | | | | | 525 |
| Thr | Thr | Asn | Pro | Arg | Lys | Leu | Tyr | Asp | Tyr | Cys | Asp | Val | Pro | Gln | Cys |
| | | | | 530 | | | | | 535 | | | | | 540 | |

```
Ala Ala Pro Ser Phe Asp Cys Gly Lys Pro Gln Val Glu Pro Lys Lys
            545                 550                 555
Cys Pro Gly Arg Val Val Gly Gly Cys Val Ala His Pro His Ser Trp
        560                 565                 570
Pro Trp Gln Val Ser Leu Arg Thr Arg Phe Gly Met His Phe Cys Gly
    575                 580                 585
Gly Thr Leu Ile Ser Pro Glu Trp Val Leu Thr Ala Ala His Cys Leu
590                 595                 600                 605
Glu Lys Ser Pro Arg Pro Ser Ser Tyr Lys Val Ile Leu Gly Ala His
            610                 615                 620
Gln Glu Val Asn Leu Glu Pro His Val Gln Glu Ile Glu Val Ser Arg
            625                 630                 635
Leu Phe Leu Glu Pro Thr Arg Lys Asp Ile Ala Leu Leu Lys Leu Ser
        640                 645                 650
Ser Pro Ala Val Ile Thr Asp Lys Val Ile Pro Ala Cys Leu Pro Ser
    655                 660                 665
Pro Asn Tyr Val Val Ala Asp Arg Thr Glu Cys Phe Ile Thr Gly Trp
670                 675                 680                 685
Gly Glu Thr Gln Gly Thr Phe Gly Ala Gly Leu Leu Lys Glu Ala Gln
            690                 695                 700
Leu Pro Val Ile Glu Asn Lys Val Cys Asn Arg Tyr Glu Phe Leu Asn
            705                 710                 715
Gly Arg Val Gln Ser Thr Glu Leu Cys Ala Gly His Leu Ala Gly Gly
        720                 725                 730
Thr Asp Ser Cys Gln Gly Asp Ser Gly Gly Pro Leu Val Cys Phe Glu
    735                 740                 745
Lys Asp Lys Tyr Ile Leu Gln Gly Val Thr Ser Trp Gly Leu Gly Cys
750                 755                 760                 765
Ala Arg Pro Asn Lys Pro Gly Val Tyr Val Arg Val Ser Arg Phe Val
            770                 775                 780
Thr Trp Ile Glu Gly Val Met Arg Asn Asn
            785                 790
```

THROMBIN ACTIVATABLE PLASMINOGEN ANALOGUES

CROSS REFERENCE TO RELATED APPLICATIONS

This application is a continuation-in-part of U.S. patent application Ser. No 07/854,603, filed Jun. 4, 1992.

This invention is a improvement of the invention disclosed in our copending paint application WO-A-9109118, and relates to plasminogen analogues which are activated by thrombin to have fibrinolytic activity or to inhibit blood clot formation. It also relates m nucleic acid (DNA and RNA) coding for all or part of such compounds. The invention also relates to their preparation, pharmaceutical compositions containing them and their use in the treatment of thrombotic disease.

BACKGROUND OF THE INVENTION

Plasminogen is a key component of the fibrinolytic system which is the natural counterpart to the clotting system in the blood. In the process of blood coagulation, a cascade of enzyme activities is involved in generating a fibrin network which forms the framework of a clot, or thrombus. Degradation of the fibrin network (fibrinolysis) is accomplished by the action of the enzyme plasmin. Plasminogen is the inactive precursor of plasmin and conversion of plasminogen to plasmin is accomplished by cleavage of the peptide bond between arginine 561 and valine 562 of plasminogen. Under physiological conditions this cleavage is catalysed by tissue-type plasminogen activator (tPA) or by urokinase-type plasminogen activator (uPA).

If the balance between the clotting and fibrinolytic systems becomes locally disturbed, intravascular clots may form at inappropriate locations leading to conditions such as coronary thrombosis and myocardial infarction, deep vein thrombosis, stroke, peripheral arterial occlusion and embolism. In such cases, the administration of fibrinolytic agents has been shown to be a beneficial therapy for the promotion of clot dissolution. Antithrombotic agents are also useful for the prevention of clot formation.

However, the problem with the majority of agents used for fibrinolytic treatment is that at clinically useful doses they are not thrombus specific, as they activate plasminogen in the general circulation. An alternative approach to enhancing fibrinolysis is disclosed in our copending patent application WO-A-9109118, and is based on the use of molecules activatable to have fibrinolytic activity or to inhibit clot formation. The activation is catalysed by one or more endogenous enzymes involved in blood clotting. An advantage of this approach is that thrombus selectivity of fibrinolysis or inhibition of clot formation activity is achieved by way of the thrombus-specific localisation of the activating enzyme. In particular, WO-A-9109118 discloses, inter alia, plasminogen analogues activatale to plasmin by cleavage by thrombin.

Thrombin (E. C. 3.4.21.5) is a serine protease which catalyses the proteolysis of a number of proteins including fibrinogen (A alpha and B beta chains), Factor XIII, Factor V, Factor VII, Factor VIII, protein C and antithrombin III. The structure required for recognition by thrombin appears to be partially determined by the local amino acid sequence around the cleavage site, but is also determined to a variable extent by sequence(s) remote from the cleavage site. For example, in the fibrinogen A alpha chain, residues P2 (Val), P9 (Phe) and P10 (Asp) are crucial for α-thrombin-catalysed cleavage at the Arg(16)-Gly(17) peptide bond (Ni, F. et al 1989, Biochemistry 28 3082–3094). WO-A-9109118 discloses that optimum for alpha-thrombin may have the structure (i) (SEQ ID NO: 23)

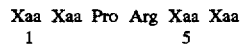

where Xaa at position 1 represents P4; Xaa at position 2 represents P3; Xaa at position 5 represents P1'; and Xaa at position 6 represents P2' where each of P3 and P4 is independently a residue of a hydrophobic amino acid (such as valine) and each of P1' and P2' is independently a non-acidic amino acid residue, or structure (ii) (SEQ ID NO:24):

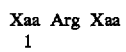

where Xaa at position 1 presents P2 and Xaa at position 3 represents P1'; where P2 or P1' is a glycine residue. Accordingly, the thrombin activatable plasminogen analogue compounds disclosed as preferred in WO-A-9109118, and all those specifically exemplified therein, have cleavage sites conforming to the foregoing structures (i) or (ii). The data reported in WO-A-910918 suggest that, of the specifically exemplified thrombin-cleavable plasminogen analogues, that designated T19 is the most effective in the assay systems used. It has a cleavage site based on Factor XIII, Pro (559) and Gly (560) of wild-type plasminogen having been replace by (SEQ ID NO:25):

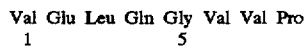

The thrombin cleavage site of T19, the most effective of the compounds specifically exemplified, therefore conforms with the requirements of structure (i) above-referenced according to WO-A-9109118.

In the absence of cofactors, Factor XI has been reported not to be cleaved by thrombin (Naito, K. and Fujikawa, K (1991), J. Biol. Chem. 266:7353–7358), or to be only slowly cleaved with a $k_{cat}/K_m = 1.6 \times 10^5 M{-}1$ min−1 (Gailani, D. and Broze, G. J. 1991, Science 253, 909–912). The cleavage site sequence of this thrombin substrate differs from the preferred general formulae i) and ii) of WO-A-9109118. In factor XI, a basic amino acid, Lys, is in the P3 position. However, although thrombin cleavage activity at this site in factor XI is very low compared to that of Factor XIII ($k_{cat}/K_m = 1.4 \times 10^5 M{-}1sec{-}1$; Naski et al;., 1991, Biochemistry 30 934–941), it has now been found in accordance with this invention, that plasminogen analogues having a thrombin cleavage sequence with a basic amino acid residue in the P3 position have surprisingly increased activity compared to T19. Such novel analogues are cleaved more rapidly by thrombin, and exhibit increased activity in a linked chromogenic assay. More significantly, such analogues are active in a plasma clot lysis assay, which more closely resembles conditions in vivo.

A further example of a thrombin cleavage site where P3 is a basic amino acid residue is found in single-chain urokinase, where P3 is arginine. Cleavage at this site produces inactive two-chain urokinase (Ichinose et al., (1986) J. Biol. Chem. 261 3486–9). In the absence of cofactors, cleavage of single-chain urokinase by thrombin is also moderately slow, with a $k_{cat}/K_m = 3.8 \times 10^4 M{-}1$ sec−1;(de Munk et al., 1990 Fibrinolysis 4 161); however, plasminogen analogues bearing the urokinase cleavage site have now been shown to have increased activity compared to T19.

SUMMARY OF THE INVENTION

Accordingly, the present invention is an improvement of the invention disclosed in WO-A-9109118 in that it provides a plasminogen analogue which is activatable by thrombin to have plasmin activity (as generally disclosed in WO-A-9109118) but specifically characterised in that it comprises a thrombin-cleavable site sequence (SEQ ID NO:23)

Xaa Xaa Pro Arg Xaa Xaa
1           5 where Xaa at position 1 represents P4; Xaa at position 2 represents P3; Xaa at position 5 represents P1'; and Xaa at position 6 represents P2'; wherein P3 is a residue of a basic amino acid, P4 is a residue of a hydrophobic amino acid, and each of P1' and P2' is independently a non-acidic amino acid residue, said site being cleavable by thrombin between Arg and P1'.

BRIEF DESCRIPTION OF THE DRAWINGS

The following figure are offered by way of illustration, and not by way of limitation.

FIG. 2 shows the result of a chromogenic assay comparing the activation of BB10151 and T19 by thrombin as discussed in Example 10; and FIG. 3 shows the clot lysis activity of BB10151 as discussed in Example 11.

DETAILED DESCRIPTION OF THE INVENTION

Figure 1:
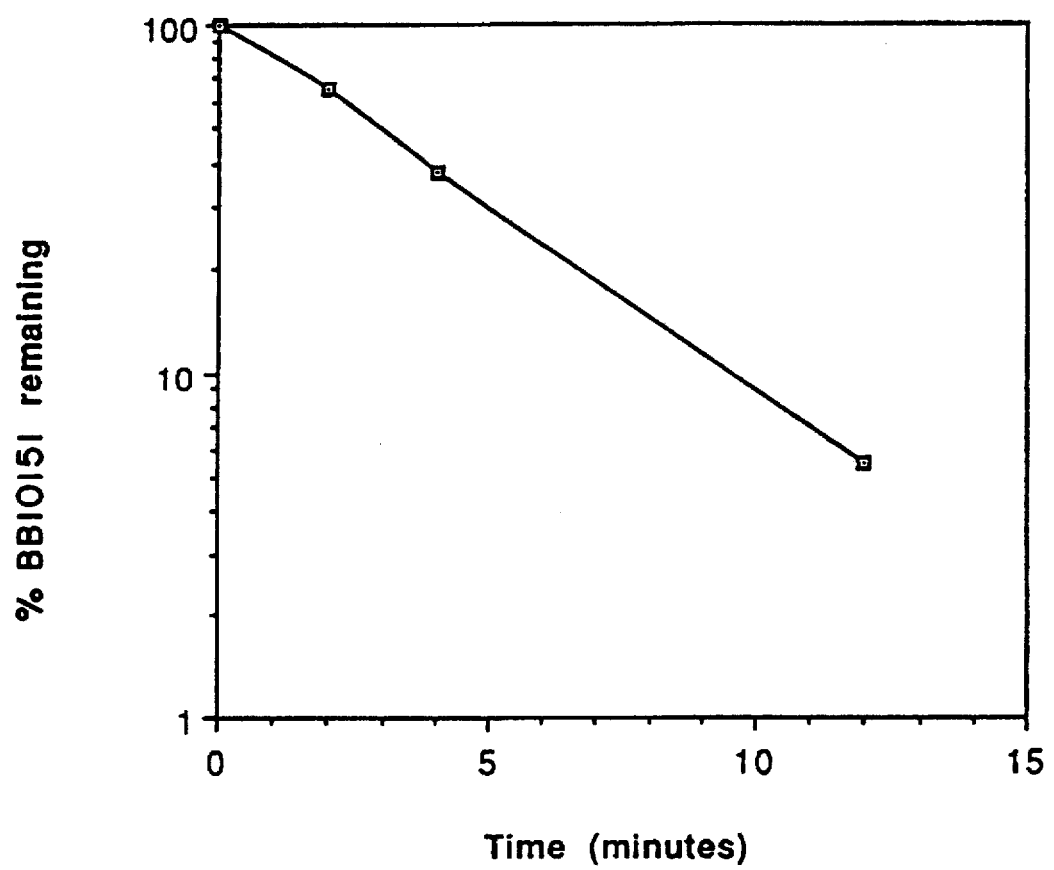
FIG. 1 shows the rate of cleavage of BB10151 by thrombin as discussed in Example 9.

Plasminogen has been numbered according to the protein sequencing studies of Sottrup-Jensen et al. (in: Atlas of Protein Sequence and Structure (Dayhoff, M. O., ed.) 5 suppl. 3, p.95 (1978)) which indicated that plasminogen was a 790 amino acid protein and that the site of cleavage was the Arg(560)-Val(561) peptide bond. However, a suitable plasminogen cDNA useful in this embodiment of the invention and that isolated by Forsgren et al (FEBS Letters 213 254–260 (1987)) code for a 791 residue protein, as shown in SEQ ID NO: 29, with an extra Ile at position 65. In this specification, the numbering of the amino acids in plasminogen corresponds to that of the cDNA used. There may be polymorphism in the structure of plasminogen and there may be forms of plasminogen in which the numbering of the cleavage site differs but it is intended that such variants be included in the embodiment.

Therefore the term "plasminogen analogue", as used in this specification, means a molecule differing from wild type plasminogen and having the ability to be cleaved or otherwise acted on to form a molecule having plasmin activity.

Plasminogen analogues within the scope of this embodiment of the invention retain the fibrin binding activity of wild type plasminogen to an adequate degree but may have altered inhibition characteristics; preferred plasminogen analogues have a plasma half life which is comparable with that of wild type plasminogen, but this property is not essential.

In the thrombin-cleavable site sequence present in plasminogen analogues according to the invention, the basic amino acid residue P3 may be a lysine or arginine residue; the hydrophobic amino acid residue P4 may be a valine, isoleucine or leucine residue; and each of the non acidic amino acid residues P1' and P2' may independently be a valine or isoleucine residue.

Particular plasminogen analogues within the scope of the invention contain the cleavage site (SEQ ID NO:26):

Thr Thr Lys Ile Lys Pro Arg Xaa Xaa
1                   5 where Xaa at position 8 represents P1' and Xaa at position 9 represents P2';, or the cleavage site (SEQ ID NO:27) Leu Arg Pro Arg
                1 where each of P1' and P2' is independently a non-acidic amino acid residue. As mentioned, P1' and P2' may be isoleucine or valine residues.

Specific and preferred compounds according to the invention are plasminogen analogues:

a) in which Pro(559), Gly(560) are replaced by Thr, Thr, Lys, Ile, Lys, Pro and Val (562) is replaced by Ile. In this analogue, amino acid 563 is valine as in the wild type. This mutant has been designated BB10151 (SEQ ID NO:1).

b) in which Cys(558), Pro(559), Gly(560) are replaced by Ala, Gly, Gln, Lys, Thr, Leu, Arg, Pro; and Cys(566) is replaced with Ala. In this analogue, amino acids 562 and 563 are valine as in the wild type. This mutant has been designated BB10156 (SEQ ID NO:10).

c) in which Cys(558), Pro(559), Gly(560) are replaced by Ala, Leu, Arg, Pro; and Cys(566) is replaced with Ala. In this analogue, amino acids 562 and 563 are valine as in the wild type. This mutant has been designated BB10170 (SEQ ID NO:12).

d) in which Pro(559), Gly(560) are replaced by Val, Glu, Leu, Gln, Gly, Leu, Arg, Pro. In this analogue, amino acids 562 and 563 are valine as in the wild type. This mutant has been designated BB10171 (SEQ ID NO:18).

e) in which Cys(558) Pro(559), Gly(560) are replaced by Ala,Thr, Thr, Lys, Ile, Lys, Pro; Val (562) is replaced by Ile; and Cys(566) is replaced with Ala This mutant has been designated BB10158 (SEQ ID NO:11).

Plasminogen analogues in accordance with the invention have been defined by particular reference to the nature of their thrombin-cleavable site sequence, since it is the surprising rapidity of cleavage at that site which underlies the improved thrombolytic activity of the compounds. However, it is likely that plasminogen analogues in accordance with the invention (i.e. containing the now identified novel cleavage site sequences) may contain other modifications (as compared with wild type plasminogen) which may be one or more additions, deletions or substitutions at sites more or less remote from the cleavage site, without losing the benefit of rapid cleavage. An example of such a modification would be the addition, removal, substitution or alteration of one or more kringle domains to alter fibrin binding activity or reduce α2-antiplasmin binding. A specific example would be mutation of the lysine-binding site located on Kringle 1 to interfere with the binding of α2-antiplasmin to this site. Such variants may be resistant to inhibition by α2-antiplasmin. Preferred embodiments include BB10189, BB10190 and BB10192, which are the plasminogen analogues BB10153, BB010170 and BB10171 respectively with the additional mutations of Asp 137>Ser and Asp 139 >Ser.

Another example would be mutation to prevent disulphide bond formation between Cys (558) and Cys (566), for example by replacing one or both of the cysteines with alanine residues, in order to remove the constraint put on the cleavage site by the disulphide bond formed between the cysteine residues. Of the preferred embodiments described above, variants BB10156, BB10158 and BB10170 have such open-loop modifications.

An example of a modification involving deletion would be lys-plasminogen variants of a plasminogen analogue in which the amino terminal 68, 77 or 78 amino acids have been deleted. Such variants may have enhanced fibrin binding activity as has been observed for lys-plasminogen compared to wild-type glu-plasminogen (Bok, R. A. and Mangel, W. F. 1985, Biochemistry 24 3279–3286). A further example involving deletion would be variants of a plasminogen analogue in which the kringle 1 or kringle 1–4 domains have been deleted to impair α2-antiplasmin binding. Such variants may be resistant to inhibition by α2-antiplasmin. Deletion of kringles 1–4 would also alter the fibrin binding and pharmokinetic properties of the molecule.

For the highly clot selective analogue of plasminogen of the present invention it may be preferred to introduce a mutation in the serine protease domain that interferes with plasmin inhibitor binding (SEQ ID NO:2 depicts the serine protease domain of wild-type plasmin, and references herein to that domain, where numbered, use the numbering of SEQ ID NO: 2). This mutation could be in a position analogous to that shown to prevent inhibitor binding to tissue plasminogen activator (Madison, E. L. et al 1989 Nature 339 721–724) or could be in another position which prevents inhibitor binding to plasminogen; such modifications are described in co-pending patent application PCT/GB 9301632, which discloses endopeptidases of the chymotrypsin superfamily which exhibit resistance to serine protease inhibitors. Such reisistance is provided by a modification in the endopeptidase or its precursor which induces one of the following a) a conformational change in the local fold of the protease;

b) a change in the relative orientations of the protease and inhibitor on forming a complex;

c) a change in the steric bulk of the protease in the region of the inhibitor, d) a change in the electrostatic potential field in the region of the inhibitor binding site; or e) any combination of the above.

A preferred embodiment is BB10158 with the A4 mutation (Glu606 to Lys) described in PCT/GB 9301632 (BB10199). This mutation is designed to interrupt ionic interactions on the surface of plasminogen, interfering with binding to antiplasmin. Mutagenesis was carried out using a 24 base oligonucleotide (SEQ ID NO:3) CTTGGGGACT TCTTCAAGCA GTGG, designed to convert Glu606 to Lys. Other preferred embodiments have, either singly or in combination, mutations at Glu606, Glu623, Phe583, Met585 or Lys 607. The Glu606 and Glu623 mutations were exemplified in PCT/GB 9301632. An example of this embodiment is BB10153 which is the plasminogen analogue BB10151 with the additional mutations of Glu606 to Lys and Glu623 to Lys.

Other plurally-modified plasminogen analogues in accordance with the invention may include one or more modifications to prevent, reduce or alter glycosylation patterns. Plasminogen analogues incorporating such modifications may have a longer half-life, reduced plasma clearance and/or higher specific activity.

Preferred features of plasminogen analogues within the scope of the invention also apply, where appropriate, to other compounds of the invention, mutatis mutandis.

The plasminogen analogues of the first aspect of the invention can be synthesised by any convenient route. According to a second aspect of the invention there is provided a process for the preparation of such a plasminogen analogue, the process comprising coupling successive amino acid residues together and/or ligating oligopeptides. Although proteins may in principle be synthesised wholly or partly by chemical means, it is preferred to prepare them by ribosomal translation, preferably in vivo, of a corresponding nucleic acid sequence. The protein may be glycosylated appropriately.

It is preferred to produce proteins of the invention by using recombinant DNA technology. DNA encoding a naturally occurring plasminogen may be obtained from a cDNA or genomic clone or may be synthesised. Amino acid substitutions, additions or deletions are preferably introduced by site-specific mutagenesis. DNA sequences encoding plasminogen analogues may be obtained by procedures familiar to those skilled in the art of genetic engineering.

The process for producing proteins using recombinant DNA technology will usually include the steps of inserting a suitable coding sequence into an expression vector and transferring the vector into a host cell. Therefore, according to a third aspect of the invention, there is provided synthetic or recombinant nucleic acid coding for a proteinaceous compound as described above. The nucleic acid may be RNA or DNA and may be in the form of a vector, such as a plasmid, cosmid or phage. The vector may be adapted to transfect or transform prokaryotic (for example bacterial) cells and/or eukaryotic (for example yeast or mammalian) cells. A vector will comprise a cloning site and usually at least one marker gene. An expression vector will have a promoter operatively linked to the sequence to be inserted in the cloning site, and, preferably, a sequence enabling the protein product to be secreted.

The plasminogen analogues of the invention may be expressed using a vector of the type described in WO-A-9109118, which comprises a first nucleic acid sequence coding for a protein or embodying a cloning site, operatively linked to a second nucleic acid sequence containing a strong promoter and enhancer sequence derived from human cytomegalovirus, a third nucleic acid sequence encoding a polyadenylation sequence derived from SV40 and a fourth nucleic acid sequence coding for a selectable marker expressed from an SV40 promoter and having an additional SV40 polyadenylation signal at the 3' end of the selectable marker sequence.

It is to be understood that the term "vector" is used in this specification in a functional sense and is not to be construed as necessarily being limited to a single nucleic acid molecule. So, for example, the first, second and third sequences of the vector defined above may be embodied in a first nucleic acid molecule and the fourth sequence may be embodied in a second nucleic acid molecule.

This vector enables the plasminogen analogues to be expressed and secreted into the cell culture medium in a biologically active form without the need for any additional biological or chemical procedures.

According to a third aspect of the invention, there is provided a process for the preparation of nucleic acid encoding the plasminogen analogues described above, the process comprising coupling successive nucleotides together and/or ligating oligo- and/or poly-nucleotides.

In a further aspect of the invention, there is provided a cell or cell line transformed by nucleic acid and/or a vector as described above. Suitable cells or cell lines to be transformed include both prokaryotic (for example Escherichia coli) and eukaryotic cells, such as yeast cells (including *Saccharomyces cerevisiae* and *Pichia pastoris*) and mammalian cells. Mammalian cells which grow in continuous culture and which can be transfected or otherwise transformed by standard techniques are preferred. Examples of suitable cells include Chinese hamster ovary (CHO) cells, mouse myeloma cell lines such as NSØ and P3X63-Ag8.653, COS cells, HeLa cells, BHK cells, melanoma cell lines such as the Bowes cell line, mouse L cells, human hepatoma cell lines such as Hep G2, mouse fibroblasts and mouse NIH 3T3 cells. CHO cells are particularly preferred as hosts for the expression of plasminogen and plasminogen analogues.

Transformation may be achieved by any convenient method; electroporation is particularly suitable.

Plasminogen analogues of the present invention may be used for the prophylaxis and/or treatment of conditions caused by an imbalance between clotting and fibrinolysis, the method comprising administering to a patient an effective amount of the plasminogen analogue. Therefore, according to a further aspect of the invention, there is provided a plasminogen analogue as disclosed herein, for use in medicine, particularly in the prophylaxis and/or treatment of conditions caused by an imbalance between clotting and fibrinolysis, where it is desired to produce local fibrinolytic and/or anticoagulant activity. Such conditions include myocardial and cerebral infarction, arterial and venous thrombosis, thromboembolism, post-surgical adhesions, thrombophlebitis and diabetic vasculopathies and coagulation imbalances associated with cancer.

The invention also provides the use of a plasminogen analogue as disclosed herein in the preparation of a thrombolytic, antithrombotic or thrombolytic antithrombotic agent.

Furthermore, there is also provided a pharmaceutical or veterinary composition comprising one or more plasminogen analogues as disclosed herein and a pharmaceutically or veterinarily acceptable carrier. Such a composition may be adapted for administration orally, by intravenous or intramuscular injection or by infusion. Suitable injectable compositions include preparations of sterile plasminogen analogue(s) in isotonic physiological saline and/or buffer and may also include a local anaesthetic to alleviate the pain of injection. Similar compositors may be used for infusion. Where the compound is to be administered as a topical treatment, it may be formulated as a cream, ointment or lotion in a suitable base.

The compounds of the invention may be supplied in unit dosage form, for example as a dry powder or water-free concentrate in a hermetically sealed container such as an ampoule or sachet.

The quantity of material to be administered will depend on the amount of fibrinolysis or inhibition of clotting required, the required speed of action, the seriousness of the thromboembolic position and the size of the clot. The precise dose to be administered will, because of the very nature of the condition which compounds of the invention are intended to treat, be determined by the physician. As a guideline, however, a patient being treated for a mature thrombus will generally receive a daily dose of a plasminogen analogue of from 0.01 to 10 mg/kg of body weight either by injection in for example up to 5 doses or by infusion.

The following Examples of the invention are offered by way of illustration, and not by way of limitation.

EXAMPLE 1

Construction Expression and Purification of BB10151

The isolation of plasminogen cDNA and construction of the vectors pGWH and pGWHgP have been described in WO-A-91/09118. In pGWHgP, transcription through the plasminogen cDNA can initiate at the HCMV promoter/enhancer and the selectable marker gpt is employed.

The techniques of genetic manipulation, expression and protein purification used in the manufacture of the modified plasminogen example to follow, are well known to those skilled in the art of genetic engineering. A description of most of the techniques can be found in one of the following laboratory manuals: "Molecular Cloning" by T. Maniatis, E. F. Fritsch and J. Sambrook published by Cold Spring Harbor Laboratory, Box 100, New York, or "Basic Methods in Molecular Biology" by L. G. Davis, M. D. Dibner and J. F. Battey published by Elsevier Science publishing Co Inc, New York.

Additional and modified methodologies are detailed in the methods section below.

BB10151 is a plasminogen analogue in which the amino acid residues Pro(559), Gly(560) are replaced by Thr, Thr, Lys, Ile, Lys, Pro and Val(562) is replaced by Ile to produce a cleavage loop clearable by thrombin (SEQ ID NO:1). This site is based on a potential thrombin cleavage site in factor XI. The procedures used in this example are essentially as described in WO-A-9109118 Examples 2 and 3, with the mutagenesis reaction carried out on the 1.87kb KpnI to HincII fragment of plasminogen cloned into the bacteriophage M13mp18. Single stranded template was prepared and the mutation made by oligonucleotide directed mutagenesis. In this case a 48 base long oligonucleotide (SEQ ID NO:4) CACCCCCCTA CGATTCTAGG TTTAATTTTA GTTGTACATT TCTTCGGC; was used to direct the mutagenesis.

Plasmid DNA was introduced into CHO cells by electroporation using 800 V and 25 µF. Selective medium containing 250 µl/ml xanthine, 5 µg/ml mycophenolic acid, 1× hypoxanthine-thymidine (HT)) was added to the cells 24 hours post transfection and the medium was changed every two to three days. Plates yielding gpt-resistant colonies were screened for plasminogen production using an ELISA assay. Cells producing the highest levels of antigen were re-cloned and the best producers scaled up into flasks with production being carefully monitored. Frozen stocks of all these cell lines were laid down. Producer cells were scaled up into roller bottles to provide conditioned medium from which plasminogen protein was purified using lysine SEPHAROSE 4B. (The word SEPHAROSE is a trade mark.) The cell line used to produce this mutant protein was 123.C6.

EXAMPLE 2

Construction of BB10153

BB10153 is a derivative of BB10151 (SEQ ID NO:1) containing two additional mutations (Glu606 to Lys and Glu623 to Lys) to impair binding of α2-antiplasmin. The 663bp EcoRV to Sph I fragment of BB10151 (SEQ ID NO:1) (cloned in pUC - see Example 1) was removed and replaced with the equivalent 663bp fragment from the antiplasmin resistant mutant A3A4. Construction of this is described in example 5 of PCT/GB9301632. The 24 base oligonucleotide 5'CTT GGG GAC TTC TTC AAG CAG TGG3'(SEQ ID NO: 3), was used to convert Glu-606 to Lys and the 27 base oligonucleotide (SEQ ID NO:5): GTTCGAGATT CACTTTTTGG TGTGCAC; was used to convert Glu623 to Lys. The full length plasminogen was then cloned into the expression vector pGW1H prior to the insertion of the gpt selection marker as described in WO-A-9109118 Example 2.

EXAMPLE 3

Construction of BB10156(SEQ. ID NO10), BB10158 (SEQ ID NO:11) & BB10170 (SEQ ID NO:12)

The DNA encoding plasminogen mutant BB10150 was used as the template for production of BB10156 (SEQ. ID NO10), BB10158 (SEQ ID NO:11) & BB10170 (SEQ ID NO:12). BB10150 is a plasminogen analogue in which the amino acid residues Pro(559), Gly(560) are replaced by Val, Val, Pro and has the additional mutations Cys(558) to Ala and Cys(566) to Ala to prevent disulphide bond formation. The opened cleavage loop sequence of BB10150 is shown in SEQ ID NO:6. BB10150 was made by mutagenesis using two oligonucleotide primers (SEQ ID NO:7): CTAGGTA-CAA CCGCTTTCTT CGGCT and (SEQ ID NO:8): GGTGGGCCAC CGCCCCCCCC AC and the 1.87kb; KpnI to HincII fragment of mutant T13 (see patent application WO-A-9109118, Example 13 and SEQ ID NO:9) cloned into M13.

Plasminogen analogues BB10156(SEQ. ID NO:10), BB10158 (SEQ ID NO:11) & BB10170 (SEQ ID NO:12) were all constructed by site specific mutagenesis using the previously described mutant BB10150 in M13 as the template so that they all have the same Cys to Ala mutations at residues 558 and 566. BB10156 (SEQ ID NO:10) is a plasminogen analogue in which the amino acid residues Pro(559), Gly(560) are replaced by Gly, Gln, Lys, Thr, Leu, Arg, Pro (SEQ ID NO:10). BB10158 is a plasminogen analogue in which the amino acid residues Pro(559), Gly (560) are replaced by Thr, Thr, Lys, Ile, Lys, Pro and Val(562) is replaced by Ile (SEQ ID NO:11). BB10170 is a plasminogen analogue in which the amino acid residues Pro(559), Gly(560) are replaced by Leu, Arg, Pro (SEQ ID NO:12). The oligonucleotides used to prime each mutagenesis are shown below:

| MUTANT OLIGONUCLEOTIDE SEQUENCE |
|---|
| BB10156  SEQ ID NO:13 |
| CAACCCTAGG TCTAAGTGTT TTCTGACCCG CTTTCTTCG |
| BB10158  SEQ ID NO:14 |
| CAACCCTAGG TTTGATCTTC GTTGTCGCTT TCTTCG |
| BB10170  SEQ ID NO:15 |
| CACAACCCTA GGTCTAAGCG CTTTCTTCGG |

In each case, following DNA sequencing, the mutation was cloned directly into the pGW1Hg.plasminogen expression vector using the restriction enzymes HindIII and SplI. These sites had previously been introduced at the extreme 5'end of plasminogen and at 1850 respectively via mutagenesis; the plasminogen amino acid coding sequence was not affected by this procedure.

EXAMPLE 4

Construction of BB10169 and BB10171

BB10169 is a plasminogen analogue in which the amino acid residues Pro(559), Gly(560) are replaced by Val, Glu, Leu, Gln, Gly, Ile, Lys Pro and Val (562) is replaced by Ile (SEQ ID NO:16). BB10169 was made by oligonucleotide directed mutagenesis of BB10151 in M13 using the 42 base oligonucleotide (SEQ ID NO:12) GATTCTAGGT TTAAT-GCCCT GCAGTTCCAC ACATTTCTTC GG; followed by cloning into pGW1Hg plasminogen using HindIII and SplI. BB10171 is a plasminogen analogue in which the amino acid residues Pro(559), Gly(560) are replaced by Val, Glu, Leu, Gln, Gly, Leu, Arg, Pro (SEQ ID NO:18). The single stranded M13 from BB10169 was used as the template for the construction of BB10171. Mutagenesis was primed using the 39 base oligonucleotide (SEQ ID NO:19) CAC-CCCCCTA CCACTCTGGG TCTCAGGCCC TGCAGT-TCC; and, following DNA sequencing, was cloned into the expression vector using HindIII and SplI.

EXAMPLE 5

Construction and Expression of BB10189, BB10190 and BB10191

Plasminogen analogues BB10189, BB10190 and BB10191 have the kringle 1 double mutation Asp(137) to Ser, Asp(139) to Set to disable the lysine binding site. The mutation was performed in the BB10153, BB10170 and BB10171 backgrounds (see examples 2, 3 & 4) using the 28 base long oligonucleotide (SEQ ID NO:20) CCCTGCG-GAG AGTTGGATGG ATTCCTGC; The mutation was then cloned into pGW1Hg.plasminogen using the restriction enzymes HindIII and SplI.

EXAMPLE 6

Construction of BB10181

BB10181 has the cleavage site sequence of BB10170 and an additional mutation of Phe(583) to Arg to interfere with the binding of α2-antiplasmin. BB10181 was constructed via an intermediate BB10150-based construct using M13 containing full length BB10150 as the template and the oligonucleotide (SEQ ID NO:21) GAAGTGCATT CCTCTCCTCG TACGAAG as the primer; The mutated BB10150 gene was then cloned into pGW1Hg using the restriction enzymes HindIII and SmaI. The BB10181 expression vector was then made from this intermediate by replacing the HindIII to SplI fragment from this plasmid with the corresponding portion from BB10170 (see example 3).

EXAMPLE 7

Construction of BB10186

BB10186 has the cleavage site sequence of BB10171 and an additional mutation of Met(585) to Arg to interfere with the binding of α2-antiplasmin. BB10186 was made in a similar manner to that described in example 6 above for BB10181. The intermediate BB10150 construct was made using the 25 base long oligonucleotide (SEQ ID NO:22) CCACAGAAGT GTCTTCCAAA CCTCG followed by cloning; into pGW1Hg. BB10186 was then made by a fragment switch using the HindIII to SplI fragment from BB10171 (see example 4).

EXAMPLE 8

Construction of BB10199

BB10199 has the cleavage site sequence of BB10158 and an additional mutation of Glu(606) to Lys to interfere with the binding of α2-antiplasmin. BB10199 was made essentially as described in PCTGB 9301632 examples 2 & 3. The KpnI to EcoRV fragment of a BB10158 (see example 3, above) was used to replace the corresponding fragment of a BB1051 Glu(606) to Lys construct cloned into pUC and was then cloned into the final expression vector as described in PCTGB 9301632.

EXAMPLE 9

Cleavage of BB10151

Plasminogen mutants (12.5 µg) were incubated with 2.8 µg thrombin as described in Method 1. The time course of cleavage of the plasminogen mutants was determined by quantitative gel scanning; 50% cleavage times for T19 and BB10151 were 9 and 3 minutes respectively. Gel scan data for cleavage of BB10151 are shown in FIG. 1.

EXAMPLE 10

Activation of BB10151

Purified BB10151 protein was assayed for activation using the linked chromogenic assay (see Method 2.1). Results of this assay are shown in FIG. 2 in which the increase in absorbance at 405 nm with time demonstrates that plasmin activity is generated upon incubation of BB10151 with thrombin. T19 is shown for comparison and was found to be approximately 2 times less potent than BB10151 in this assay.

EXAMPLE 11

Plasma Clot Lysis

The ability of BB10151 and T19 to lyse a plasma clot was determined as described in Method 2.2 and the results of such an assay are shown in FIG. 3. BB10151 (20 µg/ml) was able to cause complete lysis of the clot whereas T19 did not lyse the clot at concentrations up to 150p, g/ml. Thus BB10151 was found to be at least 7 times more active than T19 at inducing lysis of a plasma clot. Representative examples of other plasminogen analogues of the invention were compared for plasma clot lysis activity at a concentration of 40 µ/ml and the results in Table 1 show that they possess similar activity to BB10151

TABLE 1

| Plasminogen Analogue | Time for 50% clot lysis (min) |
|---|---|
| BB10151 | 4.5 |
| T19 | not lysed |
| BB10158 | 12.5 |
| BB10199 | 6 |
| BB10153 | 4.1 |
| BB10171 | 4.4 |
| BB10156 | 6.6 |
| BB10170 | 3.1 |

Methods

1. Cleavage Analysis

Plasminogen analogues are assessed for susceptibility to cleavage by thrombin using SDS PAGE under reducing conditions. Typical incubation volumes of 0.125 ml in 100mM Tris HCl pH 7.4 consist of plasminogen analogue, at the concentration shown in the examples, and thrombin, at the concentration shown in the examples. Incubations are performed at 37° C. Control incubations are performed under the same conditions in the absence of thrombin. The activation reactions were stopped by precipitating the protein by the addition of trichloroacetic acid to a final concentration of 20% and standing at 4° C. for >4 hours. The precipitates were then pelleted, washed with acetone and resuspended in SDS PAGE sample buffer (0.1 m Tris pH6.8, 10% glycerol, 1% SDS, 0.5% mercaptoethanol and 0.05% bromophenol blue). The samples were analysed either on 8–25% gradient gels or 12% gels. The resulting gels were analysed using a SHIMADZU Gel Scanner which scans the gel and calculates the concentration of protein in bands by determining the area under the peaks. (The word SHIMADZU is a trade mark.) The rate of cleavage of plasminogen was thus determined by measuring the disappearance of the plasminogen band at approximately 92kDa and the appearance of the plasmin heavy chain band at approximately 66kDa.

2. Activation Analysis

2.1 Linked Chromogenic Assay

Plasminogen analogue and thrombin are incubated together in the presence of the chromogenic substrate S2251 and plasmin produced by activation directly cleaves the S2251 leading to an increase in absorbance at in a total volume of 880 µl in a buffer containing 50 mM Tris HCl, 0.1 mM EDTA, 0.005% Triton X100 and 0.1% HSA. S2251 is added to a final concentration of 0.35 mg/ml and the plasminogen analogue concentration used is 3 µg/ml. The thrombin concentration used is 4.55 NIHU/ml. Aliquots of 100 µl of the reaction are removed during incubation at 37° C. and added to 25 µl d 4% acetic acid, in microtitre plates, to stop the reaction. At the completion of the time course the plates are read on a microplate reader at a wavelength of 405 nm.

2.2 In Vitro Plasma Clot Lysis Assay

A mixture of 50 µl rabbit plasma (anticoagulated with 3.8% trisodium citrate), 50 µl APTT reagent (Instrumentation Labs) and an appropriate volume of plasminogen analogue in 0.1M Tris HCl pH 7.4 is made up to 200 µl with the same buffer in a well of a 96 well microtitre plate. A separate well contains 4.4 µl 500 mM $CaCl_2$ mixed with 50.6 µl of the same buffer. The plate is incubated at 37° C. for 30 minutes and clotting is initiated by transferring 50 µl of the $CaCl_2$ to the well containing plasminogen analogue. Progress of clot formation and dissolution is followed by measuring the absorbance at 405nm (620nm reference) at timed intervals during continued incubation at 37° C. for 1 hour.

We claim:

1. In a plasminogen having a cleavage site, the cleavage of which is catalyzed by tPA or uPA, the improvement wherein said cleavage site is replaced with a thrombin cleavage site which contains the sequence (SEQ ID NO:23):

Xaa Xaa Pro Arg Xaa Xaa
1 5 where Xaa at position 1 represents P4; Xaa at position 2 represents P3; Xaa at position 5 represents P1'; and Xaa at position 6 represents P2' and wherein P3 is a basic amino acid residue selected from lysine or arginine, P4 is a hydrophobic amino acid residue selected from valine, isoleucine or leucine, and each of P1' and P2' is independently a non-acidic amino acid residue selected from valine, isoleucine or leucine, said site being clearable by thrombin between Arg and P1'.

2. The plasminogen as claimed in claim 1 in which one or both amino acids corresponding to Cys(558) and Cys(566) of wild-type plasminogen are replaced by an alanine or serine residue(s).

3. The plasminogen as claimed in claim 1, which further comprises one or more of the following mutations:

Glu (62) to Lys or Ala, Ser (17) to Leu, Arg (19) to Glu or Ala, or Glu (45) to Lys, Arg or Ala, of the serine protease domain of wild-type plasminogen (SEQ ID NO:2).

4. The plasminogen as claimed in claim 1, which further comprises one or both of the following mutations:

Phe(583) to Arg or Met(585) to Arg.

5. The plasminogen as claimed in claim 1 which further comprises substituting the amino acid residue corresponding to Glu(606) of wild-type plasminogen with a lysine residue.

6. The plasminogen as claimed in claim 1 which further comprises deletion of the amino acid residues corresponding to the amino terminal 68, 77 or 78 residues of wild-type plasminogen.

7. The plasminogen as claimed in claim 1 further comprising one or both of the following mutations;

Asp(137) to Ser or Asp(139) to Ser.

8. The plasminogen of claim 1 which is Lys-plasminogen.

9. A pharmaceutical or veterinary composition comprising a plasminogen of claim 1 together with a pharmaceutically or veterinarily acceptable carrier.

10. The plasminogen as claimed in claim 1 wherein the basic amino acid residue P3 is a lysine residue and the hydrophobic amino acid reside P4 is isoleucine.

11. A compound as claimed in claim 10 wherein the non-acidic amino acid residues P1' and P2' are isoleucine and valine respectively.

12. A compound as claimed in claimed in claim 10 wherein the cleavage site sequence is (SEQ ID NO:28)

Cys Thr Thr Lys Ile Lys Pro Arg Ile Val Gly Gly Cys
1           5                10 and is in a position corresponding to that of the cleavage site sequence from Cys(558) to Cys(566) inclusive of wild-type plasminogen.

13. The plasminogen as claimed in claim 10 wherein the cleavage site sequence is (SEQ ID NO:11):

Ala Thr Thr Lys Ile Lys Pro Arg Ile Val Gly Gly Ala
1           5                10 and is in a position corresponding to that of the cleavage site sequence from Cys(558) to Cys(566) inclusive of wild-type plasminogen.

14. The plasminogen as claimed in claim 10 wherein the cleavage site sequence is (SEQ ID NO:16):

Cys Val Glu Leu Gln Gly Ile Lys Pro Arg Ile Val Gly Gly Cys
1           5                10              15 said cleavage site sequence being in a position corresponding to that of the wild-type plasminogen cleavage site sequence from Cys(558) to Cys (566) inclusive of wild-type plasminogen.

15. The plasminogen as claimed in claim 10 wherein the cleavage site sequence is (SEQ ID N):28):

Cys Thr Thr Lys Ile Lys Pro Arg Ile Val Gly Gly Cys
1           5                10 said cleavage site sequence being in a position corresponding to that of the wild-type plasminogen cleavage site sequence from Cys(558) to Cys (566) inclusive of wild-type plasminogen, and wherein Glu(606) and Glu(623) of wild-type plasminogen have both been substituted by lysine residues.

16. The plasminogen as claimed in claim 1 wherein the basic amino acid residue P3 is an arginine residue and the hydrophobic amino acid residue P4 is leucine.

17. The plasminogen as claimed in claim 16 wherein the non-acidic amino acid residue P1' and P2' both valine.

18. The plasminogen as claimed in claim 17 wherein the cleavage site sequence is (SEQ ID NO:18):

Cys Val Glu Leu Gln Gly Leu Arg Pro Arg Val Val Gly Gly Cys
1           5                10              15 and is in a position corresponding to that of the cleavage site sequence from Cys(558) to Cys(566) inclusive of wild-type plasminogen.

19. The plasminogen as claimed in claim 17 wherein the cleavage site sequence is (SEQ ID NO:10):

Ala Gly Gln Lys Thr Leu Arg Pro Arg Val Val Gly Gly Ala
1           5                10              15 and is in a position corresponding to that of the cleavage site sequence from Cys(558) to Cys(566) inclusive of wild-type plasminogen.

20. The plasminogen as claimed in claim 17 wherein the cleavage site sequence is (SEQ ID NO:12):

Ala Leu Arg Pro Arg Val Val Gly Gly Ala
1           5                10 and is in a position corresponding to that of the cleavage site sequence from Cys(558) to Cys(566) inclusive of wild-type plasminogen.

21. The plasminogen as claimed in claim 17 wherein the cleavage site sequence is (SEQ ID NO:18):

Cys Val Glu Leu Gln Gly Leu Arg Pro Arg Val Val Gly Gly Cys
1           5                10              15 said cleavage site sequence being in a position corresponding to that of the wild-type plasminogen cleavage site sequence from Cys (558) to Cys (566) inclusive of wild-type plasminogen, and wherein Met(585) of wild-type plasminogen has been substituted by an arginine residue.

22. A method of modifying a compound having plasminogen activity and having a cleavage site, the cleavage of which is catalyzed by tPA or uPA which comprises replacing said cleavage site with a thrombin cleavage site which contains the sequence (SEQ ID NO:23):

Xaa Xaa Pro Arg Xaa Xaa
1           5 where Xaa at position 1 represents P4; Xaa at position 2 represents P3; Xaa at position 5 represents P1'; and Xaa at position 6 represents P2' and where P3 is a basic amino acid residue selected from lysine or arginine, P4 is a hydrophobic amino acid residue selected from valine, isoleucine or leucine, and each of P1' and P2' is independently a non-acidic amino acid residue selected from valine, isoleucine or leucine, said site being cleavable by thrombin between Arg and P1'.

\* \* \* \* \*

UNITED STATES PATENT AND TRADEMARK OFFICE
CERTIFICATE OF CORRECTION

PATENT NO. : 5,688,664
DATED : November 18, 1997
INVENTOR(S) : Keith Dawson; Richard Gilbert and Michael Hunter It is certified that error appears in the above-identified patent and that said Letters Patent is hereby corrected as shown below:

At Col. 1, line 8, line 9, change "a" to --an--.

At Col. 1, line 9, change "paint" to --patent--.

At Col. 1, line 13, change "m" to read --to--.

At Col. 1, line 55, change "activatale" to read --activatable--.

At Col. 2, line 2, after "optimum" insert --cleavage sites--.

In claim 1, line 58, change "clearable" to read --cleavable--.

In claim 13, line 13, please delete the third occurrence of "Gly" so that the sequence reads --Ala Thr Thr Lys Ile Lys Pro Arg Ile Val Gly Gly Ala--.

Signed and Sealed this

Fourth Day of August, 1998

*Attest:*

BRUCE LEHMAN

*Attesting Officer*     *Commissioner of Patents and Trademarks*